United States Patent
Tropsha et al.

(10) Patent No.: US 7,305,993 B2
(45) Date of Patent: Dec. 11, 2007

(54) IMPLANTATION OF TISSUE BULKING DEVICES

(75) Inventors: Yelena G. Tropsha, Plymouth, MN (US); Chris A. Deegan, Coon Rapids, MN (US); Carole A. Tronnes, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 260 days.

(21) Appl. No.: 10/974,001

(22) Filed: Oct. 26, 2004

(65) Prior Publication Data

US 2006/0088568 A1   Apr. 27, 2006

(51) Int. Cl.
*A61B 19/00* (2006.01)
*A61F 2/04* (2006.01)

(52) U.S. Cl. .......................................... 128/897; 600/37
(58) Field of Classification Search .................. 600/19, 600/29–32, 36–37, 102; 604/57, 59, 60, 604/93.01, 500, 514; 623/1.1, 1.24–1.28, 623/1.38; 424/93, 93.01, 422, 423; 128/897–899
See application file for complete search history.

(56) References Cited

U.S. PATENT DOCUMENTS

| | | | |
|---|---|---|---|
| 6,098,629 A | 8/2000 | Johnson et al. | |
| 6,238,335 B1 | 5/2001 | Silverman et al. | |
| 6,251,063 B1 | 6/2001 | Silverman et al. | |
| 6,251,064 B1 | 6/2001 | Silverman et al. | |
| 6,335,028 B1* | 1/2002 | Vogel et al. | 424/422 |
| 6,338,345 B1 | 1/2002 | Johnson et al. | |
| 6,358,197 B1* | 3/2002 | Silverman et al. | 600/29 |
| 6,401,718 B1 | 6/2002 | Johnson et al. | |
| 6,540,789 B1 | 4/2003 | Silverman et al. | |
| 6,591,838 B2 | 7/2003 | Durgin | |
| 6,592,859 B1* | 7/2003 | Bley | 424/78.08 |
| 6,595,909 B2 | 7/2003 | Silverman et al. | |
| 6,660,301 B1 | 12/2003 | Vogal et al. | |
| 6,725,866 B2 | 4/2004 | Johnson et al. | |
| 6,755,869 B2 | 6/2004 | Geitz | |
| 6,802,868 B2 | 10/2004 | Silverman et al. | |
| 2001/0046518 A1* | 11/2001 | Sawhney | 424/486 |
| 2002/0028979 A1 | 3/2002 | Silverman et al. | |
| 2002/0052653 A1 | 5/2002 | Durgin | |
| 2002/0148475 A1 | 10/2002 | Johnson et al. | |

(Continued)

OTHER PUBLICATIONS

Lejnieks et al., "Stomach Implant for Long-Term Erythropoietin Expression in Rats," *Blood*, vol. 92, No. 3, Aug. 1, 1998, pp. 888-893.

*Primary Examiner*—Charles A. Marmor, II
*Assistant Examiner*—Christine D. Hopkins
(74) *Attorney, Agent, or Firm*—Shumaker & Sieffert, P.A.

(57) ABSTRACT

One or more tissue bulking devices are implanted to bulk a structure within a patient. The tissue bulking devices may be implanted between the structure and an adventitial layer that at least partially covers the structure, or within the adventitial layer. In some embodiments, the structure is a luminal wall that defines an inner lumen, and the bulking devices are implanted endoscopically via the lumen. In such embodiments, the tissue bulking devices may be implanted between a muscular layer of the luminal wall and an adventitial layer that at least partially covers the luminal wall, or within the adventitial layer. In exemplary embodiments, the luminal wall is the wall of the esophagus of the patient, and the tissue bulking devices are implanted proximate to the lower esophageal sphincter (LES) of the patient to treat gastroesophageal reflux disease (GERD).

14 Claims, 9 Drawing Sheets

U.S. PATENT DOCUMENTS

| | | |
|---|---|---|
| 2003/0109935 A1 | 6/2003 | Geitz |
| 2003/0158601 A1 | 8/2003 | Silverman et al. |
| 2003/0188755 A1 | 10/2003 | Milbocker |
| 2003/0192558 A1 | 10/2003 | Durgin |
| 2003/0192559 A1 | 10/2003 | Durgin |
| 2003/0196670 A1 | 10/2003 | Durgin |
| 2003/0199730 A1 | 10/2003 | Silverman et al. |
| 2004/0009224 A1 | 1/2004 | Miller |
| 2004/0019388 A1 | 1/2004 | Starkebaum |
| 2004/0037865 A1 | 2/2004 | Miller |
| 2004/0037887 A1 | 2/2004 | Bourne et al. |
| 2004/0096514 A1 | 5/2004 | Vogel et al. |
| 2005/0247322 A1 | 11/2005 | Milbocker |

* cited by examiner

IMPLANTATION OF TISSUE BULKING DEVICES

FIELD OF THE INVENTION

The invention relates to tissue bulking and, more particularly, to medical methods and systems for implantation of bulking devices.

BACKGROUND

Tissue bulking involves the implantation of bulking devices within tissue of a selected structure within a patient. By bulking the tissue of the structure, the bulking devices can alter the function of the structure. For example, bulking devices may be implanted proximate to the lower esophageal sphincter (LES) of a patient to treat gastroesophageal reflux disease (GERD). When implanted proximate to the LES, the bulking devices treat GERD by cooperating with the LES to increase the closing pressure of the LES, thereby reducing the likelihood of reflux flow of fluid from the stomach into the esophagus. As other examples, bulking devices may be implanted near the pyloric sphincter or within the fundus of the stomach to treat obesity, or proximate to a urethral or anal sphincter to treat incontinence.

Luminal walls, such as the esophageal wall, stomach wall, urethral wall and anal wall, include a plurality of layers. The layers of such luminal walls, from the inner lumen outward, include a mucosal layer, submucosal layer, and a muscular layer. Typically, bulking devices implanted within such luminal walls are implanted within the submucosal layer, or between the submucosal and muscular layers. For example, U.S. Pat. No. 6,401,718 discloses an esophageal bulking device for implantation in the submucosa in the vicinity of the LES. It has also been proposed to implant bulking devices within the muscular layer. For example, U.S. Pat. No. 6,595,909 discloses implantation of bulking devices within the muscular layer of the esophagus in the vicinity of the LES.

The submucosal layer comprises soft tissue. Consequently, bulking devices implanted within or directly beneath the submucosal layer may migrate from their intended position, and may even migrate into the mucosal layer. Devices that migrate into the mucosal layer may further migrate into the lumen and be lost, or may be lost as a result of natural sloughing of the mucosal tissue. Moreover, the pronounced protrusions into a lumen caused by bulking devices implanted within or near the submucosal layer can lead to undesirable erosion of the of the mucosal layer and contact between mucosal tissues disposed on opposite sides of the lumen. Even when implanted within the muscular layer of the luminal wall, the pronounced protrusions caused by bulking devices may lead to undesirable mucosal erosion and contact between mucosal tissues disposed on opposite sides of the lumen.

Table 1 below lists documents that disclose techniques for implantation of tissue bulking devices.

TABLE 1

| Patent Number | Inventors | Title |
| --- | --- | --- |
| 2004/0037887 | Bourne et al. | Bulking agent |
| 2004/0037865 | Miller | Obesity controlling method |
| 2004/0019388 | Starkebaum | Methods and implants for retarding stomach emptying to treat eating disorders |
| 2004/0009224 | Miller | Obesity controlling method |
| 2003/0199730 | Silverman et al. | Method for treating tissue with an implant |
| 2003/0188755 | Milbocker | Treatment for gastroesophageal disease |
| 6,755,869 | Geitz | Intragastric prosthesis for treatment of morbid obesity |
| 6,725,866 | Johnson et al. | Method for treating gastroesophageal reflux disease |
| 6,660,301 | Vogel et al. | Injectable microspheres for dermal augmentation and tissue bulking |
| 6,595,909 | Silverman et al. | Method for treating tissue with an implant |
| 6,591,838 | Durgin | Implant system and method for bulking tissue |
| 6,540,789 | Silverman et al. | Method for treating morbid obesity |
| 6,401,718 | Johnson et al. | Submucosal esophageal bulking device |
| 6,251,063 | Silverman et al. | Method for treating wall forming gastrointestinal tract |
| 6,238,335 | Silverman et al. | Method for treating gastroesophageal reflux disease and apparatus for use therewith |
| 6,098,629 | Johnson et al. | Submucosal esophageal bulking device |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, at least some of the devices and methods disclosed in the patents of Table 1 may be modified advantageously by following the teachings of the present invention.

SUMMARY OF THE INVENTION

In general, the invention is directed to medical methods and systems for implantation of tissue bulking devices to bulk a structure within a patient. More particularly, the invention is directed to medical methods and systems for implantation of one or more bulking devices between the structure and an adventitial layer that at least partially covers the structure, or within the adventitial layer. In exemplary embodiments, the structure is a luminal wall that defines an inner lumen, such as an esophageal wall, stomach wall, urethral wall, or anal wall. In such embodiments, the tissue bulking devices may be implanted between a muscular layer of the luminal wall and an adventitial layer that at least partially covers the luminal wall, or within the adventitial layer.

Various embodiments of the present invention may provide solutions to one or more problems existing in the prior art with respect to prior techniques for implantation of tissue bulking devices. Such problems include, by way of example, migration and loss of bulking devices implanted within or directly beneath a submucosal layer. Additional problems include the pronounced protrusions into a lumen caused by bulking devices implanted within or below the submucosal layer, or within a muscular layer below the submucosal layer. Such protrusions can lead to undesirable mucosal tissue erosion and contact between mucosal tissues disposed on opposite sides of the lumen.

Various embodiments of the present invention may be capable of solving at least some of the foregoing problems. For example, medical methods and systems according to some embodiments provide for implantation of bulking devices between a muscular layer of a luminal wall and an adventitial layer that at least partially covers the luminal wall, or within the adventitial layer. Bulking devices implanted in these locations may be less likely to migrate than bulking devices implanted within or directly beneath a submucosal layer. Further, bulking devices implanted in these locations may cause less pronounced protrusions into a lumen, which may reduce the likelihood of mucosal erosion and contact between mucosal tissues across the lumen relative to known implantation locations.

Various embodiments of the invention may possess one or more features for solving at least some of the aforementioned problems in the existing art. In some embodiments, a method for bulking tissue of a luminal wall comprises endoscopically implanting one or more bulking devices via the lumen defined by the luminal wall. Accordingly, in some embodiments, a system for implantation of bulking devices within a luminal wall includes an endoscopic delivery device. The endoscopic delivery device may include a distal deployment system configured and sized to penetrate through the luminal wall in order to deploy a bulking device between the luminal wall and the adventitial layer, or within the adventitial layer.

In some embodiments, for example, a distal portion of the endoscopic delivery device defines a cavity, and the system further includes a vacuum port to draw a portion of the luminal wall into the cavity. The system may also include a needle that is deliverable via the endoscopic delivery device into the cavity to form a hole in the portion of the luminal wall disposed in the cavity. In exemplary embodiments, a distal end of the needle is delivered along a path that is substantially parallel to the luminal wall and substantially perpendicular to a depth of the cavity, and the depth of the cavity is sufficient such that the needle is delivered to a location that is between a muscular layer of the luminal and an adventitial layer, or within the adventitial layer. For example, the depth of the cavity may be greater than approximately 4 millimeters, within a range from approximately 4 millimeters to approximately 7 millimeters or, more preferably, within a range from approximately 4.6 millimeters to approximately 5.6 millimeters.

A placement tool, deliverable via the endoscopic delivery device, implants a bulking device through the hole formed by the needle. In some embodiments, the needle injects a fluid into the luminal wall to create an implantation pocket between the muscular and adventitial layers, or within the adventitial layer. In such embodiments, the placement tool implants the bulking device in the implantation pocket.

In exemplary embodiments, the endoscopic delivery device is sized for introduction into an esophagus of a patient, and a plurality of bulking devices are implanted within the esophageal wall of a patient proximate to the LES to treat GERD. The bulking devices cooperate with the LES to increase the closing pressure of the LES, thereby reducing the likelihood of reflux flow of fluid from the stomach into the esophagus. The bulking devices may also interact with a flap valve near the LES, or cause fibrosis within or near the LES, which may further reduce the likelihood of reflux fluid flow. The endoscopic delivery device may be steerable to allow a plurality of bulking devices to be implanted at various angles about the lumen defined by the esophageal wall, such as four bulking devices implanted at approximately 90 degree intervals about the lumen.

The bulking devices may have a predetermined form, such as a substantially cylindrical form with blunt, a traumatic edges. In some embodiments, the bulking devices are expandable after implantation, e.g., have a first, smaller size for ease of implantation, and expand to a second, larger size that provides a desired amount of tissue bulking. In exemplary embodiments, the bulking devices include a hydrogel material to provide expandability. Bulking devices including hydrogel are implanted with the hydrogel in an at least partially dehydrated state. Upon implantation, the hydrogel rehydrates to expand the size of the bulking device.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
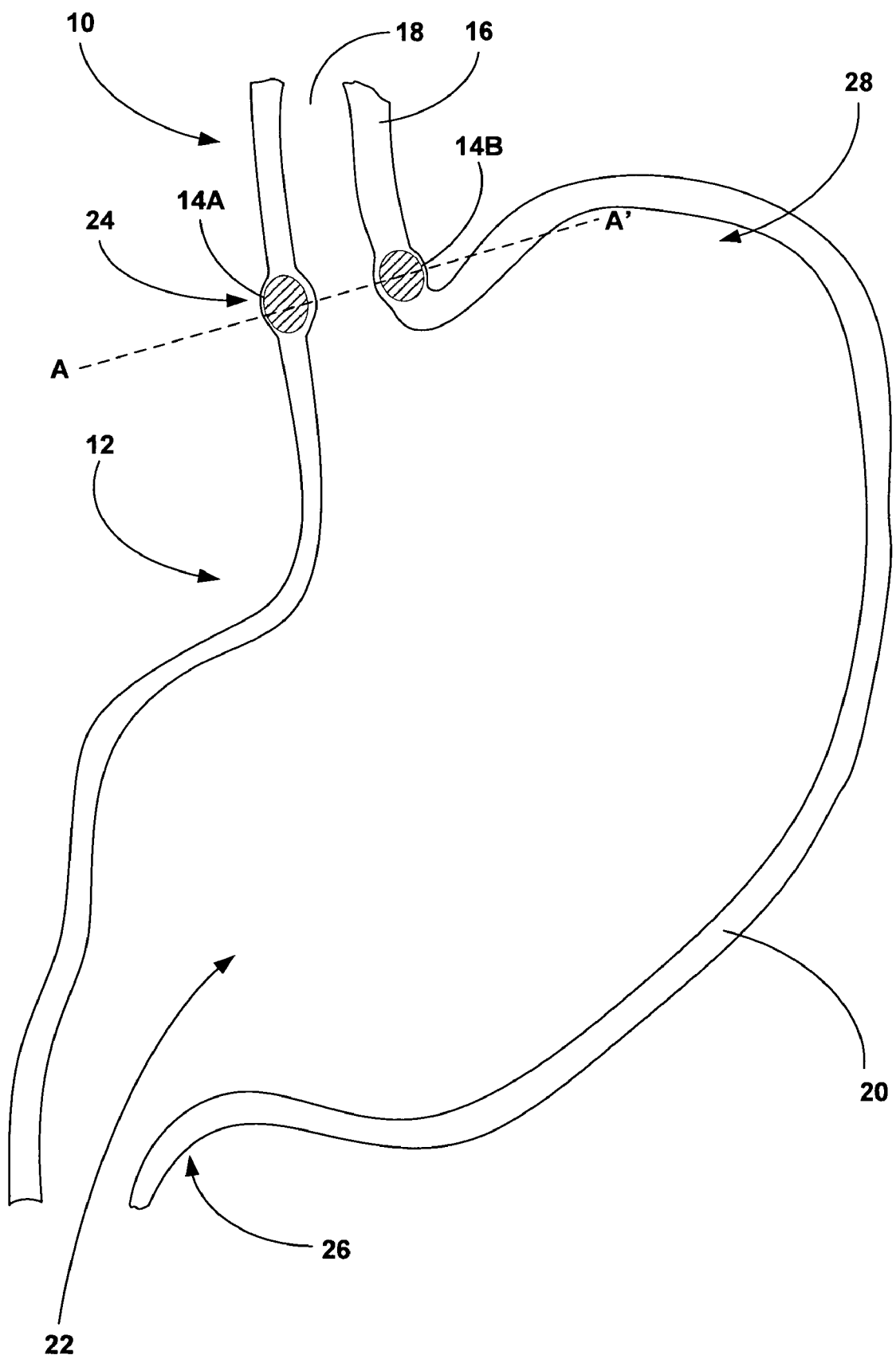
FIG. 1 is a cross-sectional diagram of an esophagus and stomach illustrating an example implantation of tissue bulking devices to bulk a wall of the esophagus.

FIG. 1 is a cross-sectional diagram of an esophagus 10 and stomach 12 illustrating an example implantation of tissue bulking devices 14A and 14B (collectively "bulking devises 14") to bulk a wall 16 of esophagus 10. In some embodiments, as will be described in greater detail below, bulking devices 14 are implanted between a luminal wall within a patient, such as esophageal wall 16, and an adventitia or adventitial layer (not shown in FIG. 1) that at least partially covers the luminal wall. In other embodiments, bulking devices 14 are implanted within the adventitial layer. Implantation of bulking devices 14 at either of these locations may provide desired bulking of a structure, while avoiding problems associated with implantation of bulking devices 14 within or between the various layers of a luminal wall. Such problems may include migration or loss of bulking devices 14, mucosal erosion, and contact between mucosal tissues across an inner lumen defined by the luminal wall.

Bulking devices 14 may be implanted surgically, e.g., lapriscopically. More preferably, bulking devices 14 that bulk a luminal wall are implanted endoscopically through the inner lumen defined by the luminal wall. In some embodiments, for example, bulking devices 14 are endoscopically implanted via one or both of esophageal lumen 18 defined by esophageal wall 16, and stomach lumen 22 defined by stomach wall 20.

Endoscopic implantation of bulking devices 14 via the lumen can prevent substantial trauma and recovery time otherwise associated with surgical implantation techniques. Endoscopic implantation may reduce the duration and complexity of the implantation procedure, and possibly eliminate the need for an overnight hospital stay in some instances. In addition, endoscopic implantation may be less likely to disrupt the physiological function of the luminal wall and other structures near the implantation site. Endoscopic implantation of bulking devices 14, and devices and systems therefor, are discussed in greater detail below.

In the illustrated embodiment, bulking devices 14 are implanted proximate to the lower esophageal sphincter (LES) 24 of the patient to treat gastroesophageal reflux disease (GERD). When implanted proximate to LES 24, bulking devices 14 cooperate with the LES to increase its closing pressure, thereby reducing the likelihood of reflux flow of fluid from stomach 12 into esophagus 10. Bulking devices 14 may also interact with a flap valve (not shown) within stomach 12 near LES 24, or cause fibrosis within or near LES 24, which may further reduce the likelihood of reflux fluid flow. Although FIG. 1 illustrates two bulking devices 14 in cross-section, a single bulking device 14 may be implanted at LES 24 or, preferably, additional bulking devices may be implanted at LES 24 at different angular positions about the esophageal lumen 18 to form a ring-like arrangement of bulking devices for treatment of GERD.

However, the invention is not limited to implantation of bulking devices 14 proximate to LES 24 or treatment of GERD. To treat obesity, for example, bulking devices 14 may be implanted some distance above LES 24 to form an obstruction of esophagus 10, proximate to pyloric sphincter 26 to impede emptying of stomach 12, or within a fundal region 28 of stomach 12 to bias stretch receptors and provide a sensation of satiety. Further, bulking devices 14 may bulk luminal walls other than esophageal wall 16 and stomach wall 20. For example, bulking devices 14 may be implanted proximate to a urethral sphincter of a urethral wall, or proximate to an anal sphincter to bulk an anal or rectal wall, to treat incontinence. Moreover, the invention is not limited to implantation of bulking devices 14 to bulk luminal walls. Bulking devices 14 may be implanted between any structure within a patient and an adventitial layer that at least partially covers the structure, or within the adventitial layer, to bulk the structure.

In the illustrated embodiments, bulking devices 14 have a predetermined form, i.e., are substantially solid when implanted. In other embodiments, however, bulking devices 14 may be formed by injecting one or more fluid materials into an implant site that solidify in situ to form a bulking device. Bulking devices 14 are illustrated herein as having substantially elliptical, cylindrical, or rod-like shapes with blunt, a traumatic edges. However, bulking devices 14 may have any regular or irregular shape.

Bulking devices 14 may be formed from an expandable material that is initially implanted with a reduced, unexpanded size. Upon implantation, bulking devices 14 expand to a larger size to provide a desired degree of tissue bulking. As an example, bulking devices 14 may be a prosthesis formed from a hydrogel material that is implanted in an at least partially dehydrated state having a reduced size. Upon rehydration following implantation, bulking devices 14 assume an expanded state and increased size. Hence, the initial, unexpanded size of bulking devices 14 facilitates implantation, but subsequent expansion provides the desired degree of tissue bulking.

Figure 2A:
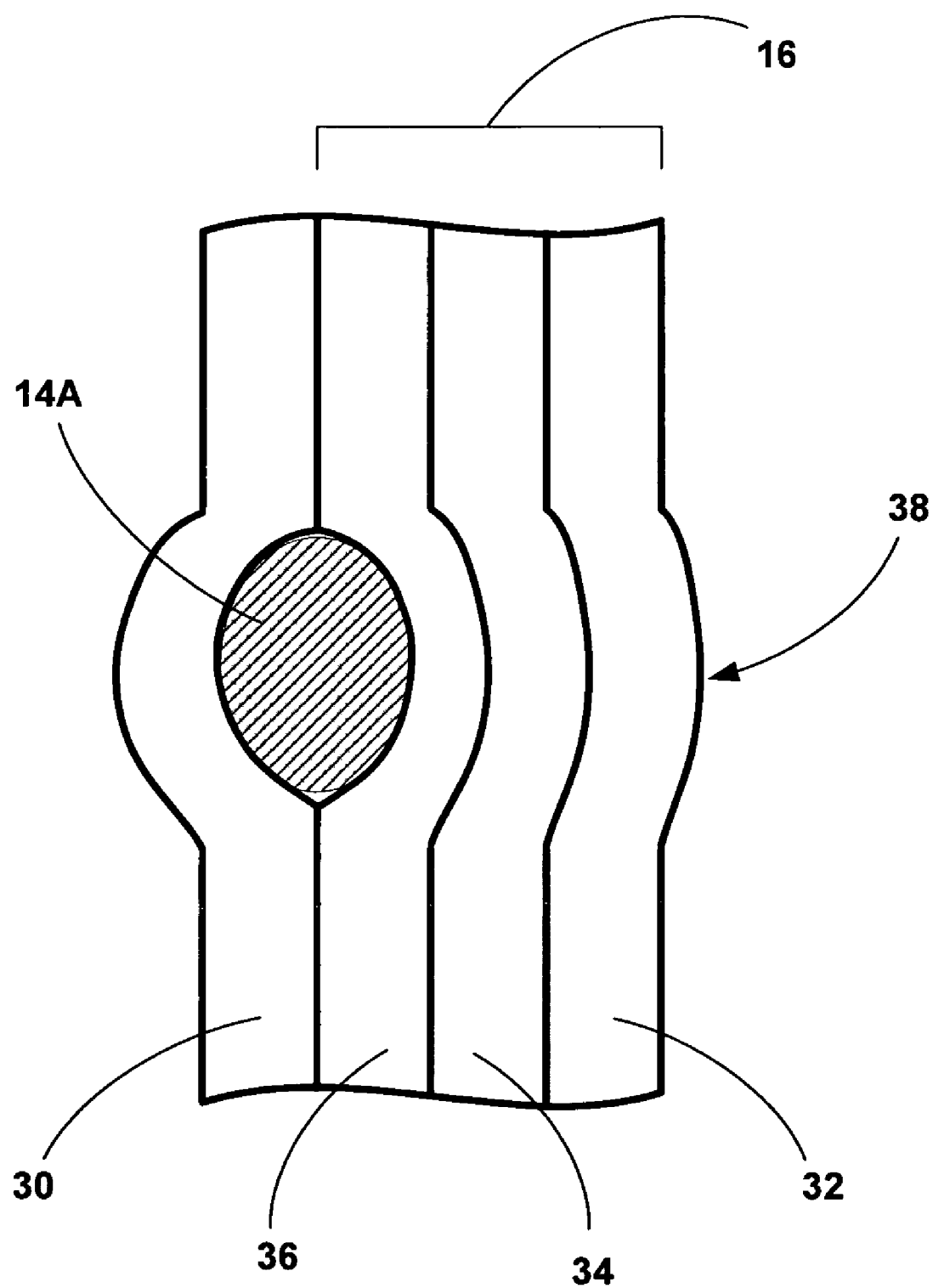
FIGS. 2A and 2B are cross-sectional diagrams of a portion of the esophageal wall further illustrating implantation of a tissue bulking device according to alternative embodiments of the invention.
Figure 2B:
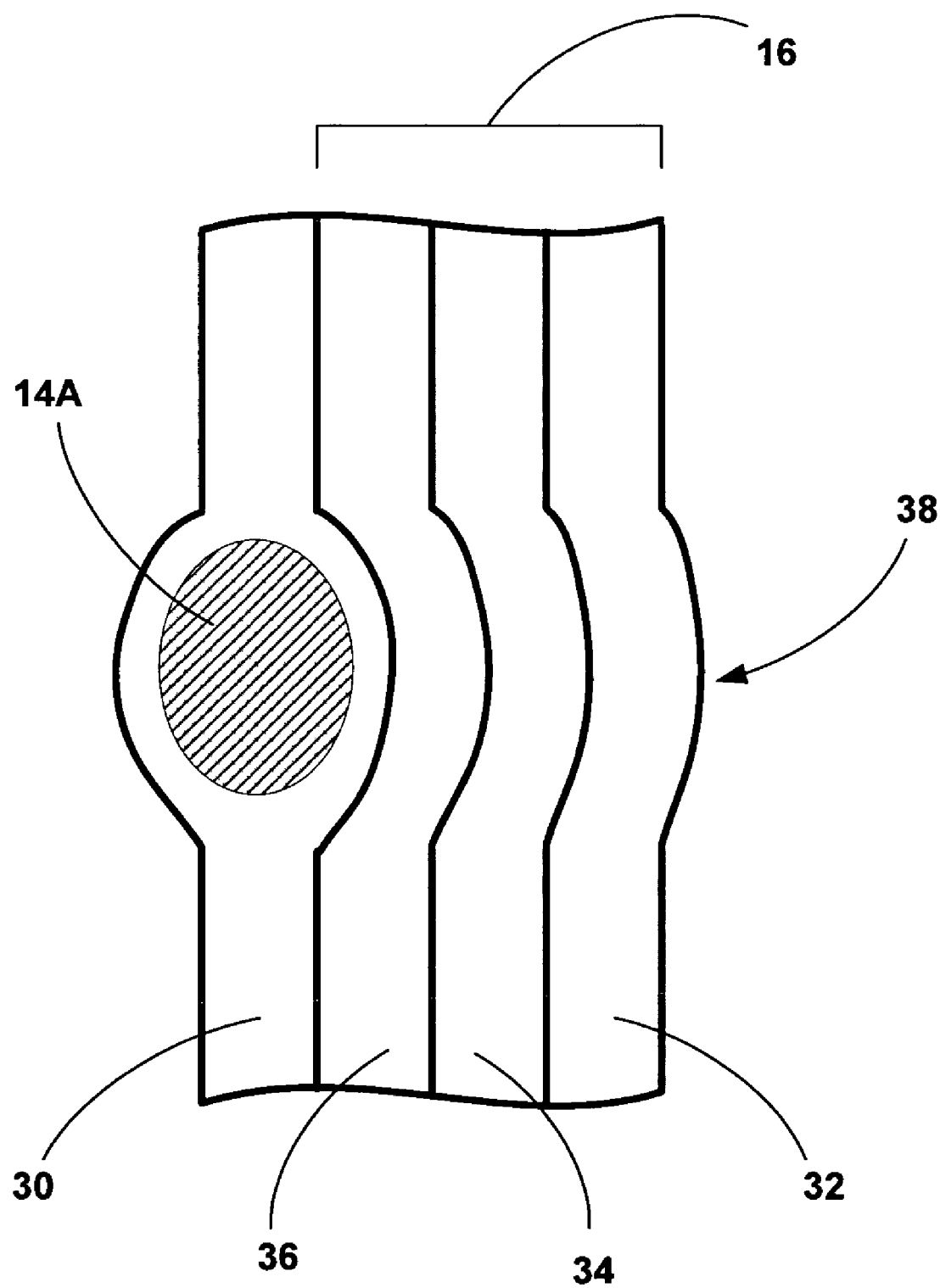

FIGS. 2A and 2B are cross-sectional diagrams of a portion of esophageal wall 16 further illustrating implantation of tissue bulking device 14A according to alternative embodiments of the invention. FIGS. 2A and 2B show the adventitia or adventitial layer 30 that at least partially covers the exterior of the esophageal wall 16. FIGS. 2A and 2B also show the layers of esophageal wall 16 which, from esophageal lumen 18 (not shown in FIGS. 2A and 2B) outward, include a mucosal layer 32, submucosal layer 34, and muscular layer 36. FIG. 2A illustrates an embodiment in which bulking device 14A is implanted between adventitial layer 30 and esophageal wall 16 and, more particularly, between adventitial layer 30 and muscular layer 36. FIG. 2B illustrates an alternative embodiment in which bulking device 14A is implanted within adventitial layer 30.

Due to variations in the thickness of layers 32-36 across a population of patients, the depth relative to esophageal lumen 18 that bulking devices are implanted in order to be located between muscular layer 36 and adventitial layer 30 or within adventitial layer 30 may vary. In general, implantation of bulking devices 14 at either of the locations illustrated by FIGS. 2A and 2B will involve implantation to a depth that is greater than approximately 1.5 millimeters. In exemplary embodiments, bulking devices 14 may be implanted at a depth that is within a range from approximately 2 millimeters to approximately 2.5 millimeters.

Adventitial layer 30 comprises connective tissue, and is thin relative to layers 32-36 of esophageal wall 18. Because connective tissue and muscular tissue are denser than submucosal tissue, bulking devices 14 implanted as illustrated in FIGS. 2A and 2B are less likely to migrate or be lost than bulking devices 14 implanted within submucosal layer 34 or between submucosal layer 34 and muscular layer 36. Also, because bulking devices 14 implanted as illustrated in FIGS. 2A and 2B are further from mucosal layer 32 than bulking devices 14 implanted within esophageal wall 16. Consequently, bulking devices 14 implanted as illustrated in FIGS. 2A and 2B may cause a less pronounced protrusion 38 into the esophageal lumen 18 and exert less pressure on mucosal layer 32, thereby reducing the likelihood of erosion of mucosal layer 32 and contact between portions of the mucosal layer across esophageal lumen 18.

Figure 3:
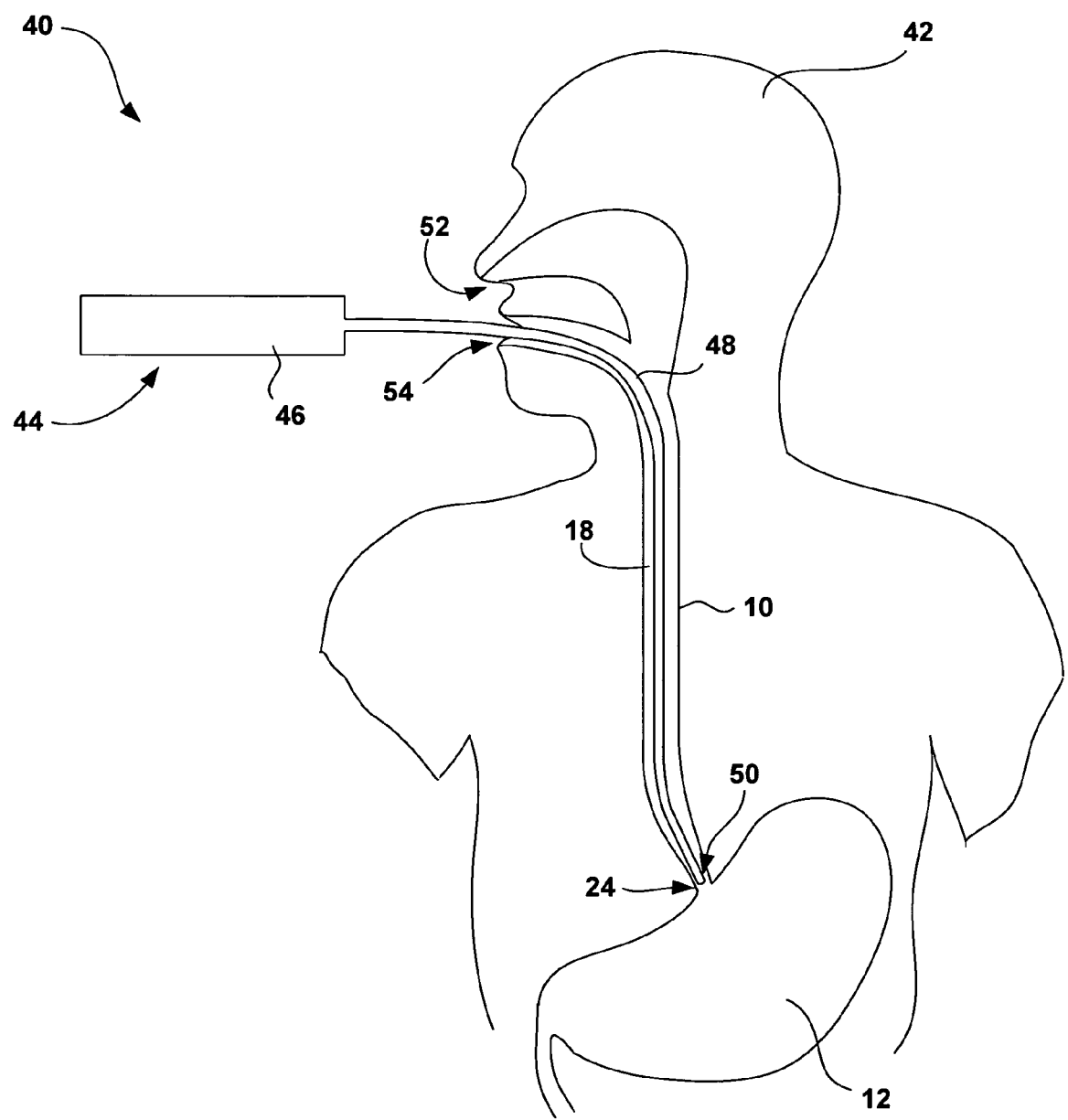
FIG. 3 is a conceptual diagram illustrating deployment of an endoscopic delivery system for implantation of tissue bulking devices shown in conjunction with an esophagus and stomach of a patient.

FIG. 3 is a conceptual diagram illustrating deployment of an endoscopic delivery system 40 for implantation of tissue bulking devices 14 shown in conjunction with esophagus 10 and stomach 12 of a patient 42. As shown in FIG. 2, endoscopic delivery system 40 serves to position and implant bulking devices 14 via esophagus 10 of patient 42. Endoscopic delivery system 40 includes an endoscopic delivery device 44 having a proximal portion, referred to herein as a handle 46, and a flexible probe 48 that extends from handle 46 into the gastrointestinal tract of patient 42.

Bulking devices 14 are implanted at target locations, such as proximate to LES 24, via a distal portion 50 of flexible probe 48. Distal portion 50 of delivery device 44 enters esophagus 10, via either nasal cavity 52 or oral cavity 54, and extends into esophagus 10 to the target implantation location. Upon implantation of a bulking device 14, endoscopic delivery device 44 may be repositioned within esophagus 10 to implant other bulking devices 14. Distal portion 50 may include a distal deployment system configured and sized to penetrate through luminal wall 16 in order to deploy a bulking device between the luminal wall and adventitial layer 30, or within the adventitial layer 30, as will be described in greater detail below.

Figure 4:
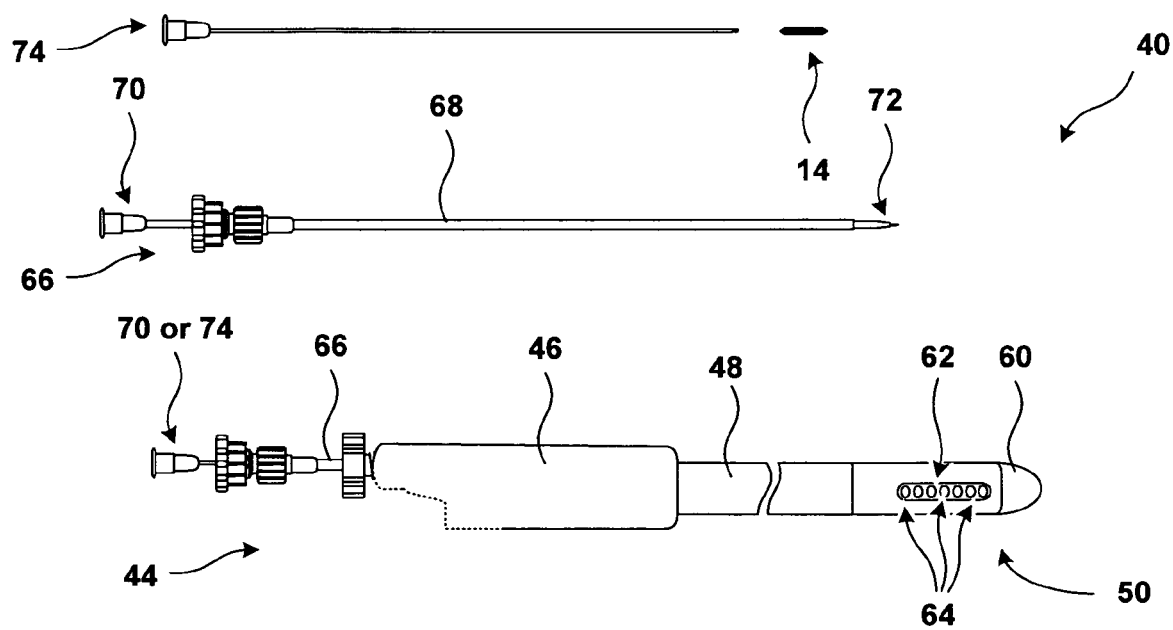
FIG. 4 is a plan view further illustrating the endoscopic delivery system of FIG. 3.

FIG. 4 is a plan view further illustrating endoscopic delivery system 40. As discussed above with reference to FIG. 3, system 40 includes endoscopic delivery device 44. Delivery device 44 houses or receives the various other components of the system, as will be described in greater detail below. Further, as discussed above with reference to FIG. 3, endoscopic delivery device 44 includes an elongated flexible portion 48 with a distal portion 50 that is positioned by a physician proximate to the target implantation location, e.g., LES 24. As shown in FIG. 4, distal portion 50 may include a blunt tip 60 that provides an a traumatic surface and that protects the tissues of the patient upon insertion of distal portion 50 into the body of patient 42. In embodiments in which bulking devices 14 are endoscopically implanted to bulk esophagus 10, flexible portion 48 and blunt tip 60 are sized for introduction into the esophagus.

Distal portion 50 defines a cavity 62 to capture tissue, such as esophageal wall 16, proximate to the target implantation site. Cavity 62 serves for positioning and implantation of bulking device 14, as described below. Cavity 62 includes a plurality of vacuum ports 64, which may be coupled to a source of vacuum pressure through the body of delivery device 44. Handle 46 may include a coupling element (not shown) to couple delivery device 44 to a source of vacuum pressure.

In FIG. 4, distal portion 50 has been rotated to make cavity 62 and vacuum ports 64 visible. In the illustrated embodiments, cavity 62 is a substantially rectangular orifice or recess with a major axis extending longitudinally relative to delivery device 44. Other shapes for cavity 62 are possible, however. In general, cavity 62 is sized and shaped to permit capture of a selected amount of tissue of a luminal wall to facilitate implantation of bulking devices 14 between a muscular layer 36 of the luminal wall and an adventitial layer 30, or within the adventitial layer. For example, the depth of cavity 62 may be chosen to facilitate implantation at these locations, as will be described in greater detail below.

A sheath assembly 66 couples to delivery device 44. Sheath assembly 66 includes a sheathe 68 that receives one or more tools that are inserted into the body of the patient through endoscopic delivery device 44. One tool that can be received in sheath 68 is a needle assembly 70. The distal end of needle assembly 70 includes a needle 72, which can penetrate and make a hole in the portion of the luminal wall drawn into cavity 62.

Another tool that can be received in sheath 68 is pushrod assembly 74. Pushrod assembly 74 is an example of a placement tool that is deliverable via endoscopic delivery device 44 to implant bulking device 14 within the tissue of patient 42. When bulking device 14 is inserted into sheath 68, pushrod assembly 74 drives bulking device 14 to the distal end of sheath 68.

In a typical application, a physician makes a hole in the portion of the luminal wall drawn into cavity 62 with needle 72, and pushes bulking device 14 through the hole with pushrod assembly 74. Bulking device 14 is shown in FIG. 4 in its unexpanded, e.g., dehydrated, state. In its unexpanded state, bulking device 14 may be more easily pushed through sheath 68 and the hole formed in the luminal wall by needle 72. Further, implantation of bulking devices 14 in an unexpanded state may allow delivery device to be more easily sized for introduction into lumen of the patient, such as esophageal lumen 18, e.g., may allow the diameter of flexible portion 48 of delivery device 44 to be reduced.

FIGS. 5-9 are cross-sectional side views of distal portion 50 of endoscopic delivery device 44 interacting with esophageal wall 16, illustrating use of endoscopic implantation system 40 to implant a bulking device 14. For ease of illustration, layers 32-36 (FIGS. 2A and 2B) of esophageal wall 16 are not depicted in FIGS. 5-9. Additionally, for ease of illustration, vacuum ports 64 (FIG. 4) and other structures used to deliver vacuum pressure from handle 46 (FIGS. 3 and 4) to cavity 62 are not depicted in FIGS. 5-9. FIGS. 5-9 illustrate implantation of a bulking device 14 between esophageal wall 16 and adventitial layer 30. However, it is understood that, in other embodiments, a system 40 may be used to implant a bulking device 14 within the adventitial layer 30, as described above.

Figure 5:
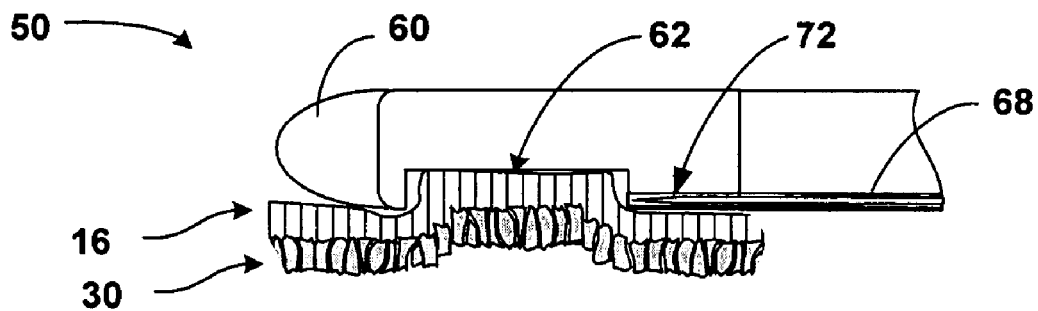
FIGS. 5-9 are cross-sectional side views of a distal portion of an endoscopic delivery device interacting with the esophageal wall, illustrating use of the system of FIG. 4 to implant a bulking device.
Figure 7:
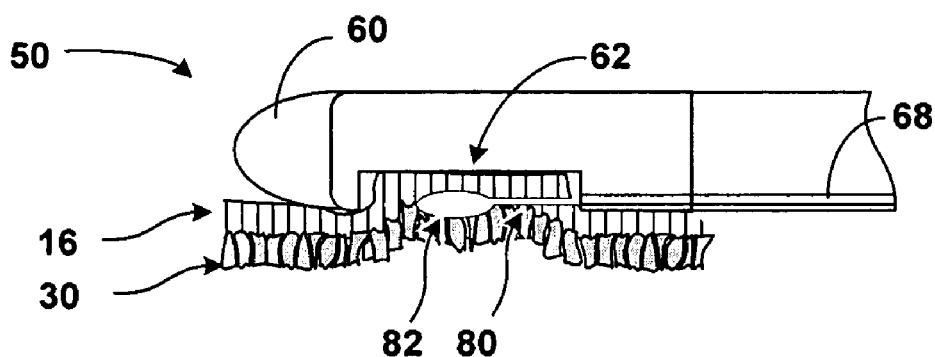
Figure 8:
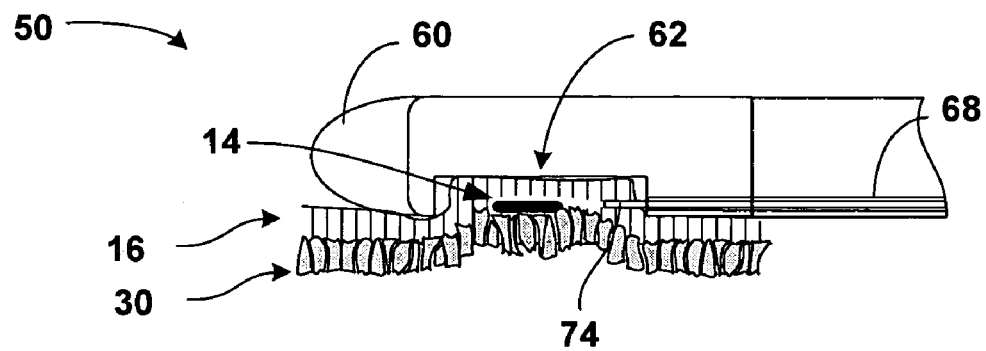

FIG. 5 depicts a portion of esophageal wall 16 drawn into cavity 62 by vacuum pressure applied to cavity 62. With the portion of esophageal wall 16 drawn into cavity 62, a physician makes a hole 80 in the esophageal wall with needle 72, as shown in FIGS. 7 and 8. The physician pushes needle assembly 70 through sheath 68, thereby advancing needle 72 into cavity 62 and making hole 80.

Figure 6:
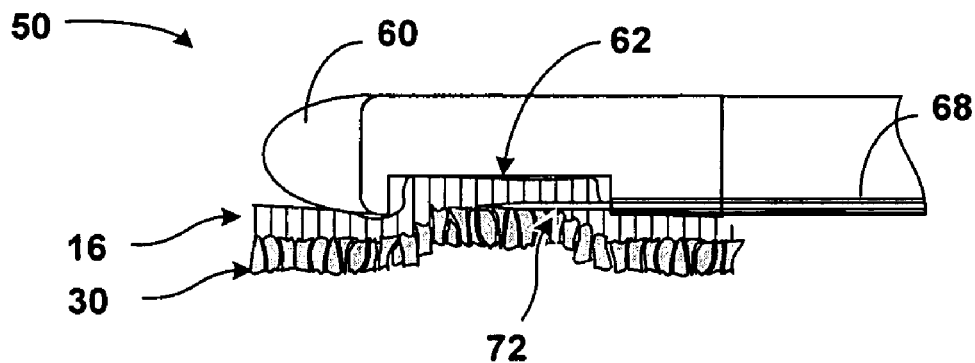

As shown in FIGS. 5 and 6, needle 72 is advanced through sheath 68 and into cavity 62 along a path that is substantially parallel to esophageal wall 16, and substantially perpendicular to the depth of cavity 62. However, as shown in FIG. 6, a portion of esophageal wall 16 is drawn sufficiently deeply into cavity 62 such that the distal end of needle 72 extends to a location between esophageal wall 16 and adventitial layer 30. In some embodiments, as shown in FIG. 7, needle 72 may inject a fluid, such as saline, to form an implantation pocket 82 between esophageal wall 16 and adventitial layer 16. In other embodiments, the portion of esophageal wall 16 is drawn sufficiently deeply into cavity 62 such that the distal end of needle 72 extends to a location within adventitial layer 30, and an implantation pocket 82 may be formed within the adventitial layer.

Figure 9:
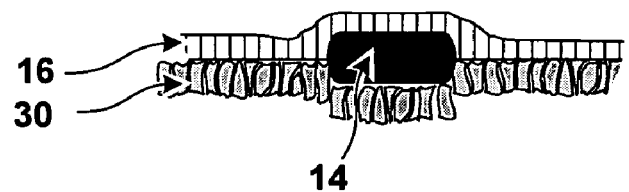

The physician withdraws needle assembly 70 from sheath 68, and inserts bulking device 14 into sheath 68. The physician pushes bulking device 14 through hole 80 and into implantation pocket 82 with pushrod assembly 74, as shown in FIG. 8. When implanted, bulking device 14 is in an unexpanded state. As shown in FIG. 9, endoscopic delivery device 44 may be withdrawn following implantation of bulking device 14. Over time, bulking device 14 expands, e.g., due to absorption of fluid from the body of patient 42. In its expanded state, bulking device 14 provides a desired degree of tissue bulking.

Figure 10:
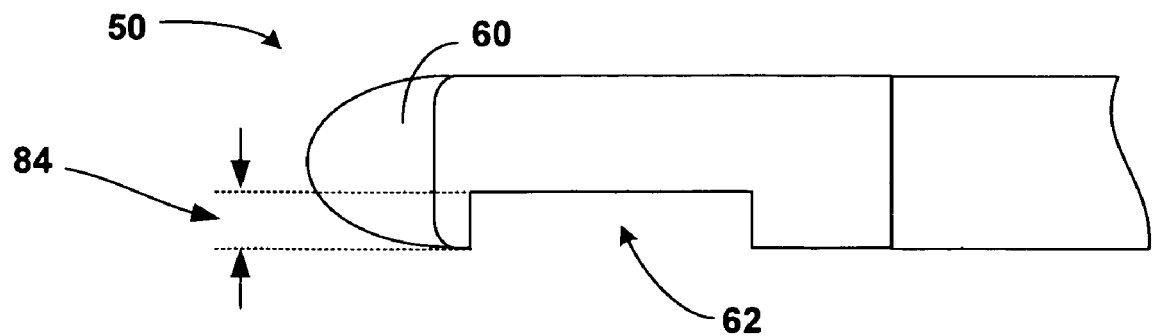
FIG. 10 is a cross-sectional side view of the distal portion of the endoscopic delivery device illustrating a cavity defined by the distal portion.

FIG. 10 is a cross-sectional side view of distal portion 50 of endoscopic delivery device 44 illustrating the cavity 62 defined by the distal portion. Cavity 62 has a depth 84 that facilitates advancement of needle 72 to a location between a luminal wall and an adventitial layer 30, or within the adventitial layer, and implantation of tissue bulking devices 14, e.g., by pushrod assembly 74, at these locations. As discussed above, in order to implant bulking devices 14 at these locations, they may be implanted at a depth relative to a lumen of greater than approximately 1.5 millimeters and, more preferably within a range from approximately 2 millimeters to approximately 2.5 millimeters. The depth of cavity 62 that facilitates implantation at these locations or depths relative to lumen may be greater than approximately 4 millimeters, within a range from approximately 4 millimeters to approximately 7 millimeters or, more preferably, within a range from approximately 4.6 millimeters to approximately 5.6 millimeters.

In addition to allowing the depth at which bulking devices 14 are implanted to be controlled, implantation of bulking devices 14 by drawing a luminal wall into cavity 62 and extending needle 72 and pushrod assembly 74 into the cavity may be safer than other implantation techniques. For example, implantation of bulking devices 14 in this manner may reduce the likelihood that a needle 72, pushrod assembly 74, or other implantation mechanism extends through the adventitial layer 30 and into other structures near the luminal wall, such as the aorta which is near esophageal wall 16.

Figure 11:
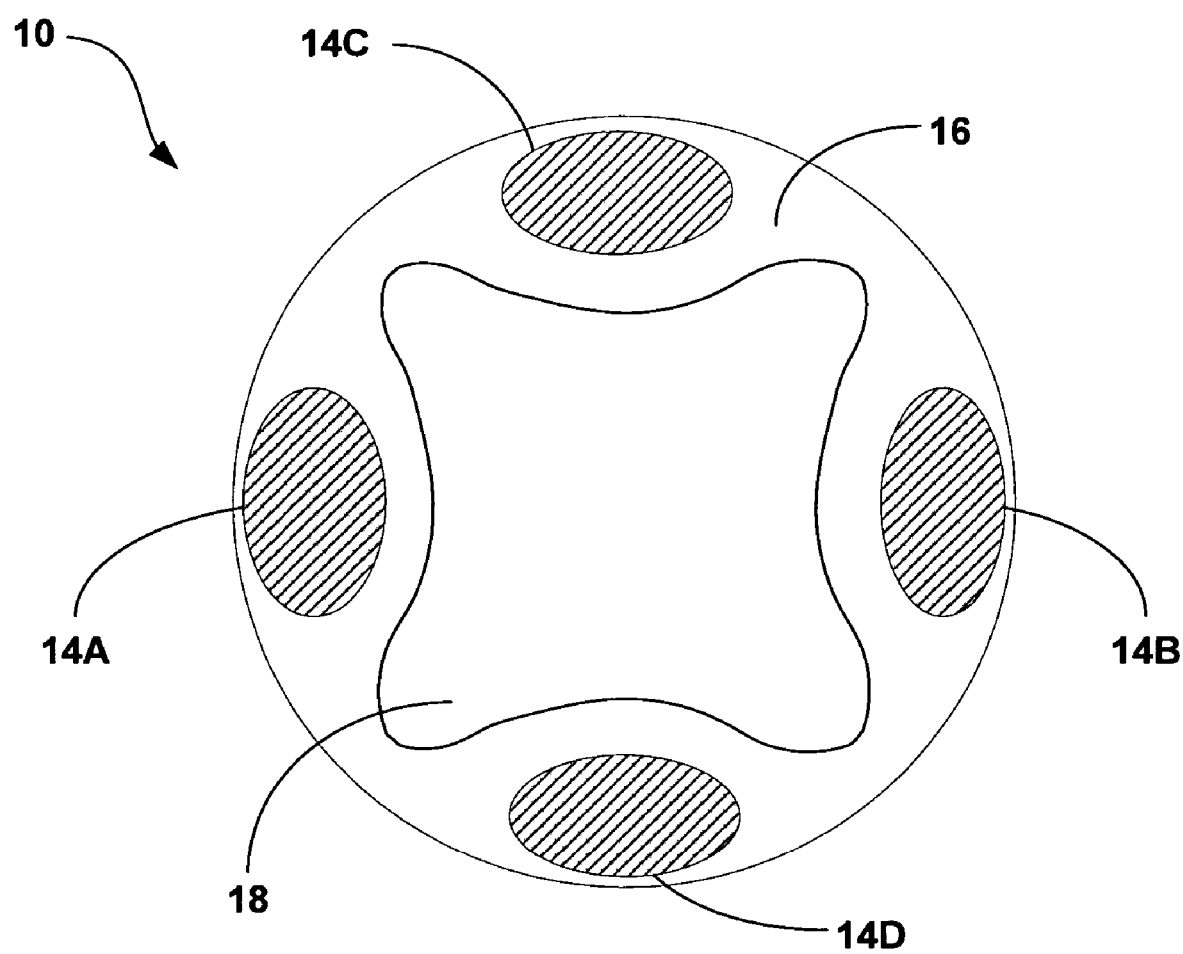
FIG. 11 is a cross-sectional end view of the esophagus taken across line A-A' of FIG. 1, illustrating implantation of a plurality of tissue bulking devices at various angles about the esophageal lumen.

FIG. 11 is a cross-sectional end view of esophagus 10 taken across line A-A' of FIG. 1, illustrating implantation of a plurality of tissue bulking devices 14 at various angles about esophageal lumen 18. In particular, FIG. 11 illustrates bulking devices 14A, 14B visible in FIG. 1 and additional bulking devices 14C, 14D implanted at approximately 90 degree intervals around esophageal lumen 18. Line A-A' of FIG. 1 is approximately parallel with the line defined by LES 24 (FIG. 1), and bulking device 14 are implanted proximate to LES 24 to treat GERD. Although a single bulking device 14 may increase the closing pressure of LES 24, and interact with LES 24 and surrounding structures to reduce the likelihood of reflux fluid flow, it may be desirable to implant a plurality of bulking devices 14 to increase the degree of improvement of LES functioning. Moreover, implantation of bulking devices 14 at various angles about esophageal lumen 18 may allow for more uniform realization of such improvements to the functioning of LES 24 about its circumference.

Figure 12:
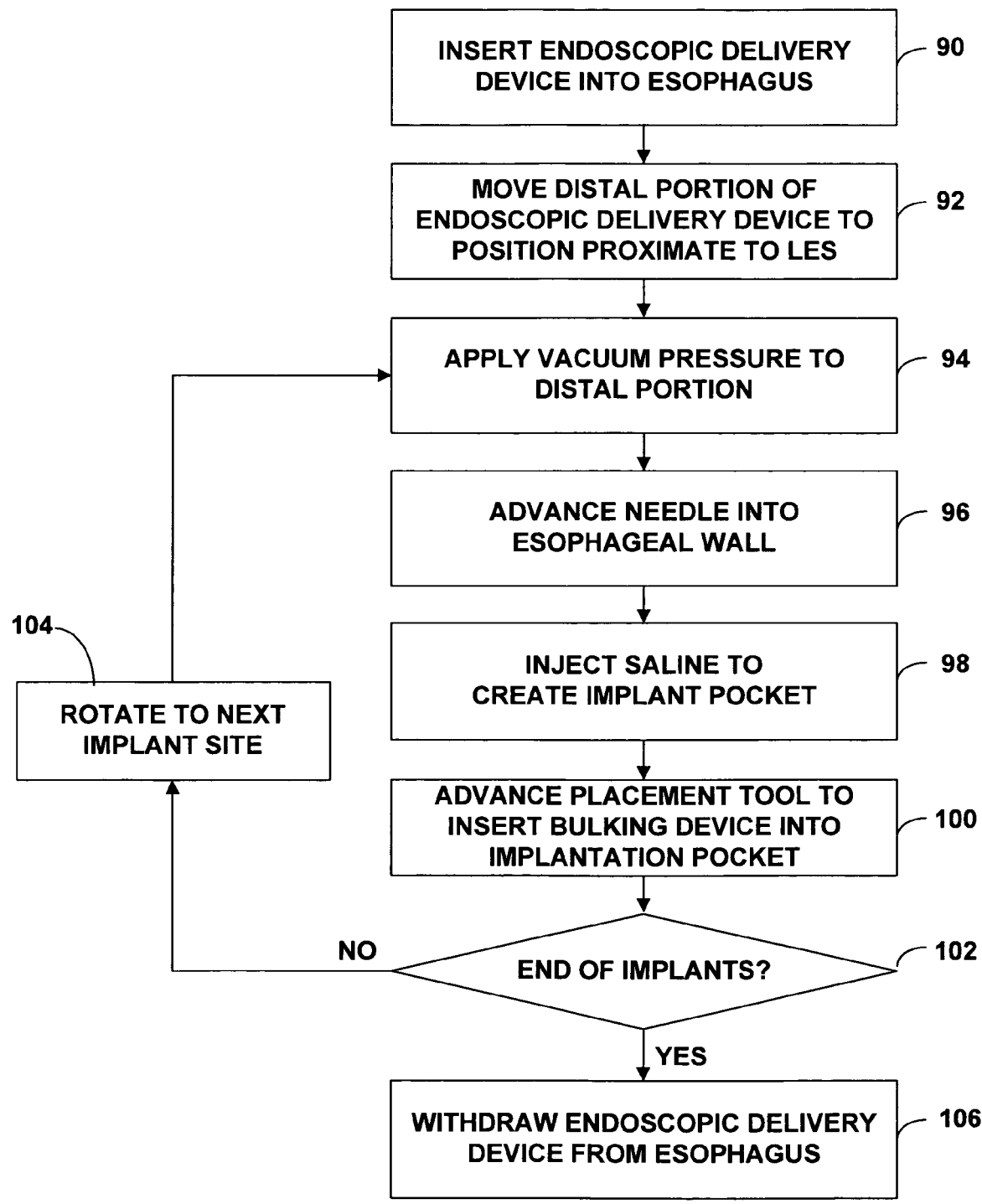
FIG. 12 is a flow diagram illustrating an example method for implanting one or more bulking devices.

FIG. 12 is a flow diagram illustrating an example method for implanting one or more bulking devices to bulk the esophageal wall of a patient proximate to the LES to, for example, treat GERD. As shown in FIG. 12, a physician inserts an endoscopic delivery device into the esophagus of the patient (90), and moves a distal portion of a flexible probe of the device to a position proximate to the LES (92). The physician then applies vacuum pressure to the distal portion to draw a portion of the esophageal wall into a cavity defined by the distal portion (94).

The physician advances a needle into the cavity to form a hole in the esophageal wall (96). A distal end of the needle is advanced along a path that is substantially parallel to the esophageal wall and perpendicular to the cavity. The needle is advanced to a position between the esophageal wall 16 and an adventitial layer, or a position within the adventitial layer. Once the distal end of the needle is in place, the physician injects saline or another fluid to create an implantation pocket (98).

The physician then withdraws the needle, and deploys a placement tool, such as a pushing rod, via the delivery device, which implants the bulking device through the hole and into the implant pocket (100). If additional bulking devices are to be implanted (102), the physician repositions the flexible probe to another implant site (104) proximate to the LES and repeats the implantation process. When all bulking devices have been implanted, the physician withdraws the endoscopic delivery device from the esophagus (106).

A bulking device 14, as described herein, preferably is soft and compliant to minimize trauma within a luminal wall upon implantation. The bulking device may be constructed from a variety of biocompatible polymeric materials. Again, the materials forming bulking device may be expandable. In particular, as described herein, the bulking devices may be formed from an expandable hydrogel material. Suitable materials, including hydrogel materials, are described in U.S. Pat. No. 6,401,718 to Johnson et al., assigned to Medtronic Endonetics, Inc., and entitled "Submucosal esophageal bulking device," the entire content of which is incorporated herein by reference.

As alternatives, described in U.S. Pat. No. 6.401,718 to Johnson et al., bulking device 14 may take the form of a fluid-filled, flexible capsule, pillow or balloon made from elastomeric materials such as silicone, latex, urethane, and the like. Example fillers include biocompatible liquid or gel such as saline, silicone oil, DMSO, polyvinyl, pyrollidone and hydrogels. As a further alternative, the bulking device may be a unitary structure formed by molding, casting, stamping or the like. The unitary structure may formed from hydrogel material, biocompatible foam material such as silicone foam or polyurethane foam, or a variety of biocompatible materials such as silicone, polyurethane, polysulfone, polyester, and the like. As described in U.S. Pat. No. 6,401,718 to Johnson et al., foam material may include outer skin of porous foam that facilitates tissue ingrowth.

As alternatives to implanted solid materials, bulking devices may be formed by injected fluids that form solids following injection. A variety of implanted solid materials and injected fluids suitable for formation of bulking devices form a partial obstruction of the esophagus, as described herein, are disclosed in U.S. Published Patent Application No. 20040019388, to Starkebaum, assigned to Medtronic, Inc. and entitled "Methods and implants for retarding stomach emptying to treat eating disorders," the entire content of which is incorporated herein by reference. Accordingly, bulking devices may refer to solid, semi-solid, or filled implants, or injected fluids that form solid or semi-solid bulking devices in situ.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems as described herein.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Several embodiments of the present invention are described above. It is to be understood that various modifications may be made to those embodiments of the present invention without departing from the scope of the claims. These and other embodiments are intended to fall within the scope of the appended claims.

The invention claimed is:

1. A method for bulking a luminal wall that defines a lumen within a patient, the method comprising:
   forming a hole in the luminal wall; and
   implanting a bulking device within an adventitial layer that at least partially covers the luminal wall through the hole.

2. The method of claim 1, wherein implanting a bulking device comprises endoscopically implanting the bulking device via the lumen.

3. The method of claim 2, wherein endoscopically implanting the bulking device comprises:
advancing a distal portion of an endoscopic delivery device through the lumen to an implantation site;
applying vacuum pressure at the distal portion of the delivery device to draw a portion of the luminal wall at the implantation site into a cavity defined by the distal portion delivery device;
advancing a needle from the delivery device into the cavity to form the hole in the portion of the luminal wall disposed in the cavity; and
implanting the bulking device within the adventitial layer through the hole.

4. The method of claim 3, further comprising injecting a fluid via the needle to create an implantation pocket within the adventitial layer, wherein implanting the bulking device comprises implanting the bulking device in the implantation pocket through the hole.

5. The method of claim 3, wherein advancing a needle comprises advancing a distal end of the needle along a path that is substantially parallel to the luminal wall and substantially perpendicular to a depth of the cavity to a location within the adventitial layer.

6. The method of claim 1, further comprising implanting a plurality of bulking devices at different angular positions about the lumen.

7. The method of claim 6, wherein implanting a plurality of bulking devices comprises implanting four bulking devices spaced at approximately 90 degree intervals from one another.

8. The method of claim 1, wherein implanting a bulking device comprises implanting the bulking device proximate to a sphincter of the patient, and the implanted bulking device cooperates with the sphincter to increase a closing pressure of the sphincter.

9. The method of claim 1, wherein the lumen comprises an esophagus of the patient.

10. The method of claim 9, wherein implanting a bulking device comprises implanting the bulking device proximate to a lower esophageal sphincter of the patient.

11. The method of claim 1, wherein implanting a bulking device comprises implanting a bulking device having a predetermined form.

12. The method of claim 11, wherein the bulking device is expandable following implantation.

13. The method of claim 12, wherein the bulking device includes a hydrogel material, and implanting a bulking device comprises implanting the bulking device with the hydrogel material in an at least partially dehydrated state, the bulking device rehydrating upon implantation and thereby expanding in size to bulk the structure.

14. The method of claim 11, wherein implanting a bulking device comprises implanting a bulking device with a substantially cylindrical shape and blunt, a traumatic edges.

* * * * *